US011707338B2

(12) United States Patent
Grimsley et al.

(10) Patent No.: US 11,707,338 B2
(45) Date of Patent: Jul. 25, 2023

(54) STORAGE SYSTEM INCLUDING AT LEAST ONE CONTAINER CONTAINING MEDICAL SUPPLIES

(71) Applicant: PAR Excellence Systems, Inc., Cincinnati, OH (US)

(72) Inventors: Rich Grimsley, Cincinnati, OH (US); Thaddeus E. MacKrell, Grosse Pointe, MI (US)

(73) Assignee: PAR Excellence Systems, Inc., Cincinnati, OH (US)

(*) Notice: Subject to any disclaimer, the term of this patent is extended or adjusted under 35 U.S.C. 154(b) by 172 days.

(21) Appl. No.: 16/262,345

(22) Filed: Jan. 30, 2019

(65) Prior Publication Data

US 2019/0231467 A1    Aug. 1, 2019

Related U.S. Application Data

(60) Provisional application No. 62/623,833, filed on Jan. 30, 2018.

(51) Int. Cl.
*A61B 50/13* (2016.01)
*A61B 17/06* (2006.01)
(Continued)

(52) U.S. Cl.
CPC ............ *A61B 50/13* (2016.02); *A47B 88/988* (2017.01); *A61B 17/06133* (2013.01);
(Continued)

(58) Field of Classification Search
CPC .............. A61B 50/13; A61B 17/06133; A61B 2050/105; A47B 88/988; A47B 2010/025;
(Continued)

(56) References Cited

U.S. PATENT DOCUMENTS 2,171,105 A * 8/1939 Wurzburg ............... A47B 63/02
312/348.3
5,193,891 A * 3/1993 Headley ............... A47B 81/068
312/348.3
(Continued)

FOREIGN PATENT DOCUMENTS

CN    206639302 U    3/2017
CN    107301749 A    7/2017

OTHER PUBLICATIONS

Annex to Form PCT/ISA/206 Communication Relating to the Results of the Partial International Search and Provisional Opinion Acompanying the Partial Search Result for International Patent App. No. PCT/US2019/015829 dated Mar. 15, 2019; 8 pages.
(Continued)

*Primary Examiner* — Randy W Gibson
(74) *Attorney, Agent, or Firm* — Frost Brown Todd LLP; Vance V. VanDrake, III

(57) ABSTRACT

A storage system includes at least one cabinet, a plurality of shelves adjustably positioned within the at least one cabinet, and a plurality of scales removably attached to at least one of the shelves, each of the scales including a load sensor. The storage system also includes a plurality of holders, each of the holders being configured to hold at least one container containing medical supplies, and each of the holders being supported by a respective one of the scales. The storage system also includes a receiver in operative communication with each of the load sensors. Each of the load sensors is configured to continuously measure a weight of the medical supplies contained in the respective at least one container held by the respective holder, and to communicate each detected weight to the receiver.

13 Claims, 6 Drawing Sheets

(51) Int. Cl.
*G01G 19/52* (2006.01)
*G06Q 10/08* (2012.01)
*A47B 88/988* (2017.01)
*A47F 10/00* (2006.01)
*A61B 50/10* (2016.01)
*G06Q 10/087* (2023.01)
*A47F 10/02* (2006.01)

(52) U.S. Cl.
CPC ........ *G01G 19/52* (2013.01); *A47F 2010/025* (2013.01); *A61B 2050/105* (2016.02); *G06Q 10/087* (2013.01)

(58) Field of Classification Search
CPC ...... G06Q 10/087; G01G 19/52; G01G 21/28; G01G 21/22; A47F 2010/025
See application file for complete search history.

(56) References Cited

U.S. PATENT DOCUMENTS

| | | | |
|---|---|---|---|
| 6,576,849 B2 | 6/2003 | Bliss et al. | |
| 6,639,156 B2 * | 10/2003 | Luke | G01G 19/4144 177/25.13 |
| 7,166,821 B2 * | 1/2007 | Adamski | A47J 39/00 126/21 A |
| 7,665,326 B2 * | 2/2010 | LeClear | F25D 23/003 62/441 |
| 9,275,361 B2 * | 3/2016 | Meyer | G01G 19/42 |
| 9,557,209 B2 * | 1/2017 | Savage | G01G 19/42 |
| 9,773,092 B2 | 9/2017 | Olson et al. | |
| 9,911,048 B2 * | 3/2018 | Jones | A47F 5/0043 |
| 10,001,402 B1 * | 6/2018 | Gyori | G06Q 10/087 |
| 10,064,502 B1 * | 9/2018 | Gyori | G01G 21/28 |
| 10,121,121 B1 * | 11/2018 | De Bonet | A47B 57/406 |
| 10,373,118 B1 | 8/2019 | Lefkow et al. | |
| 10,466,095 B1 * | 11/2019 | O'Neill | G01G 19/4144 |
| 10,540,553 B2 * | 1/2020 | Jones | A47F 5/0043 |
| 10,732,026 B1 * | 8/2020 | Danenberg | H01R 12/725 |
| 2001/0034671 A1 * | 10/2001 | Luke | G06Q 10/087 705/28 |
| 2002/0057042 A1 * | 5/2002 | Milligan | A47B 88/49 312/334.46 |
| 2002/0178066 A1 | 11/2002 | Roh et al. | |
| 2003/0047603 A1 * | 3/2003 | Lustenberger | G01G 19/42 235/385 |
| 2005/0113970 A1 | 5/2005 | Holmes et al. | |
| 2006/0190130 A1 | 8/2006 | Fedor et al. | |
| 2008/0183599 A1 | 7/2008 | Hill et al. | |
| 2009/0222359 A1 | 9/2009 | Henry | |
| 2011/0139871 A1 | 6/2011 | Yturralde et al. | |
| 2012/0200385 A1 | 8/2012 | Savage et al. | |
| 2014/0201041 A1 * | 7/2014 | Meyer | G01G 19/42 705/28 |
| 2014/0201042 A1 * | 7/2014 | Meyer | G06Q 10/087 705/28 |
| 2015/0366377 A1 | 12/2015 | Savage et al. | |
| 2016/0048798 A1 * | 2/2016 | Meyer | G01G 19/4144 705/28 |
| 2016/0247118 A1 | 8/2016 | Singh | |
| 2016/0304280 A1 | 10/2016 | Elazary et al. | |
| 2017/0217011 A1 | 8/2017 | Savage et al. | |
| 2020/0202137 A1 * | 6/2020 | Li | G07G 1/14 |
| 2020/0219371 A1 * | 7/2020 | Mizuno | G08B 13/2462 |
| 2022/0104636 A1 * | 4/2022 | Chila | G16H 40/20 |

OTHER PUBLICATIONS

International Search Report and Written Opinion of the International Searching Authority for International Patent App. No. PCT/US2020/043887 dated Oct. 6, 2020; 6 pages.

International Search Report and Written Opinion for International Application No. PCT/US2019/015829, International Search Report dated Jun. 27, 2019; 14 pages.

* cited by examiner

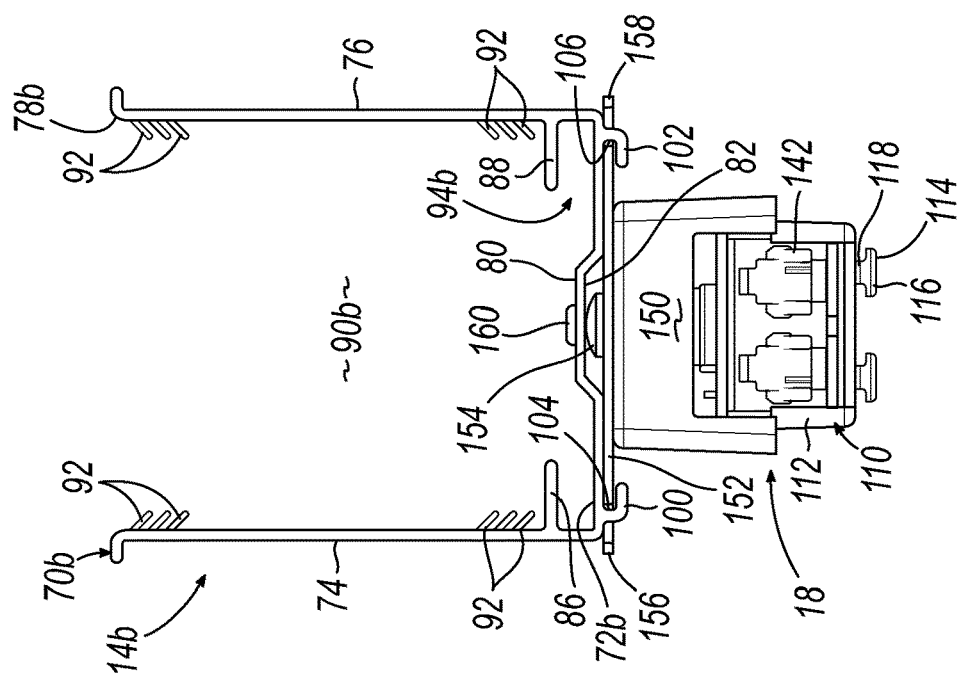
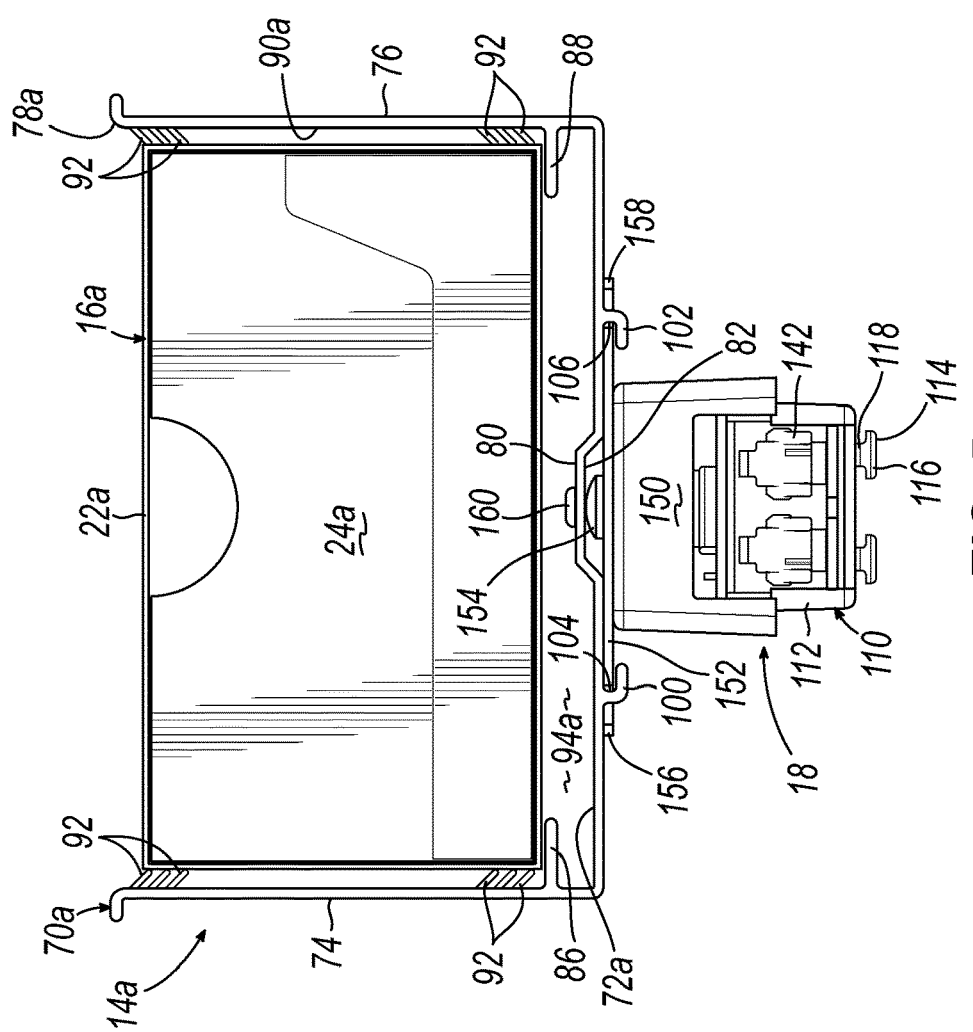

STORAGE SYSTEM INCLUDING AT LEAST ONE CONTAINER CONTAINING MEDICAL SUPPLIES

CROSS REFERENCE TO RELATED APPLICATION

This application claims the benefit of U.S. Provisional Patent Application Ser. No. 62/623,833, filed on Jan. 30, 2018, the disclosure of which is incorporated by reference herein in its entirety.

FIELD OF THE INVENTION

The invention relates to a system for storing supplies in standardized containers, with an inventory monitoring feature.

BACKGROUND OF THE INVENTION

In a variety of physical locations, medical supplies must be able to be stored and accessed. For example, nursing facilities, medical offices, and hospitals, among others, have ongoing needs for supplies having medical-related applications. For example, in a hospital having operating room capabilities, sutures are regularly required by the surgeon. Depending upon the nature of the surgery, a variety of sutures must be readily available for use by the surgeon undertaking the medical procedure. Further, a still more specialized grouping of sutures can be required in an individual operating arena, to be immediately available during the course of a surgery. Thus, sutures used in performing joint replacements will be of a different size and composition than those used in delicate neurosurgery. As a result, though a central core storage area in an operating room center may contain a wide range of sutures, in the individual operating room a much more specific suture selection is needed.

There exists a need for a system which efficiently stores and monitors inventories of sutures, both in a central operating room storage area, and in an individual operating room for a selected type of surgery.

SUMMARY OF THE INVENTION

In one embodiment, a storage system includes at least one cabinet, a plurality of shelves adjustably positioned within the at least one cabinet, and a plurality of scales removably attached to at least one of the shelves, each of the scales including a load sensor. The system also includes a plurality of holders, each of the holders being configured to hold at least one container containing medical supplies, and each of the holders being supported by a respective one of the scales. The system further includes a receiver in operative communication with each of the load sensors. Each of the load sensors is configured to continuously measure a weight of the medical supplies contained in the respective at least one container held by the respective holder, and to communicate each detected weight to the receiver. The receiver may be configured to monitor an inventory condition of the medical supplies contained in each of the at least one container held by each holder in response to each detected weight. For example, the receiver may be configured to display the inventory condition to a monitoring station.

Each of the holders may include a plurality of longitudinally extending resilient finger grips for frictionally engaging the respective at least one container. In addition or alternatively, each of the holders may include a storage slot configured to receive one or more of the medical supplies which have been removed from the respective at least one container. In one embodiment, each of the holders is longitudinally slidable relative to the respective scale. For example, the storage system may further include a plurality of support plates, each of the support plates being supported by a respective one of the scales, wherein each of the holders slidably receives the respective support plate. Each of the holders may include a stop hole and each of the support plates may include a flexible tab configured to releasably engage the stop hole of the respective holder for limiting longitudinal sliding of the respective holder relative to the respective scale.

The plurality of holders may include a first plurality of holders each having a first width, and a second plurality of holders each having a second width less than the first width. In addition or alternatively, each of the scales may include a plurality of mounting feet and each of the shelves may include a plurality of mounting holes, each of the mounting holes being configured to receive a respective one of the mounting feet. In one embodiment, the at least one cabinet is mounted to a mobile cart. In another embodiment, the at least one cabinet includes a plurality of cabinets mounted on a rack. In yet another embodiment, the at least one cabinet includes a plurality of cabinets interconnected in a matrix and mounted on a stand.

In another embodiment, a medical supply holder includes a U-shaped frame having a bottom wall and first and second side walls spaced apart from each other to define an opening, wherein the bottom wall includes a longitudinally extending ridge defining a longitudinally extending bottom channel. The medical supply holder also includes first and second longitudinally extending box supports positioned on interior sides of the first and second side walls, respectively, at an aligned height. The first and second side walls and first and second box supports collectively define a main cavity which is sized and configured to receive at least one container containing medical supplies. The bottom wall, first and second side walls, and first and second box supports may collectively define a storage slot configured to receive one or more of the medical supplies which have been removed from the at least one container.

The medical supply holder may further include first and second longitudinally extending hook-shaped rails positioned on an exterior side of the bottom wall, such that the bottom wall and the first and second rails define first and second longitudinally extending grooves configured to slidably engage a support plate of a scale. In addition or alternatively, at least one stop hole may be provided in the ridge to assist in retaining the holder on a scale. In one embodiment, the frame is constructed of a plastic material.

The medical supply holder may also include a plurality of longitudinally extending resilient finger grips positioned on interior sides of the first and second side walls for frictionally engaging the at least one container. The finger grips may be constructed of a plastic material having a hardness of approximately 40 Shore A.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the invention.

FIG. 5 is a front elevation view of the suture holder and suture scale of FIG. 4.

FIG. 6 is a front elevation view of an alternative suture holder locked in place relative to the respective suture scale.

DETAILED DESCRIPTION OF THE INVENTION

Figure 2:
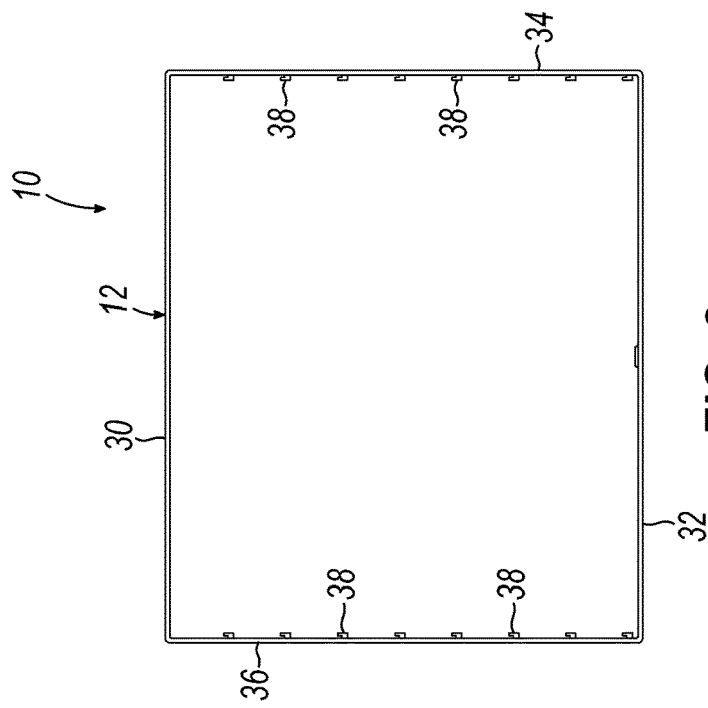
FIG. 2 is a front elevation view of the storage cabinet of FIG. 1, showing the shelves and contents thereof removed from the storage cabinet to illustrate the shelf supports of the storage cabinet.
Figure 1:
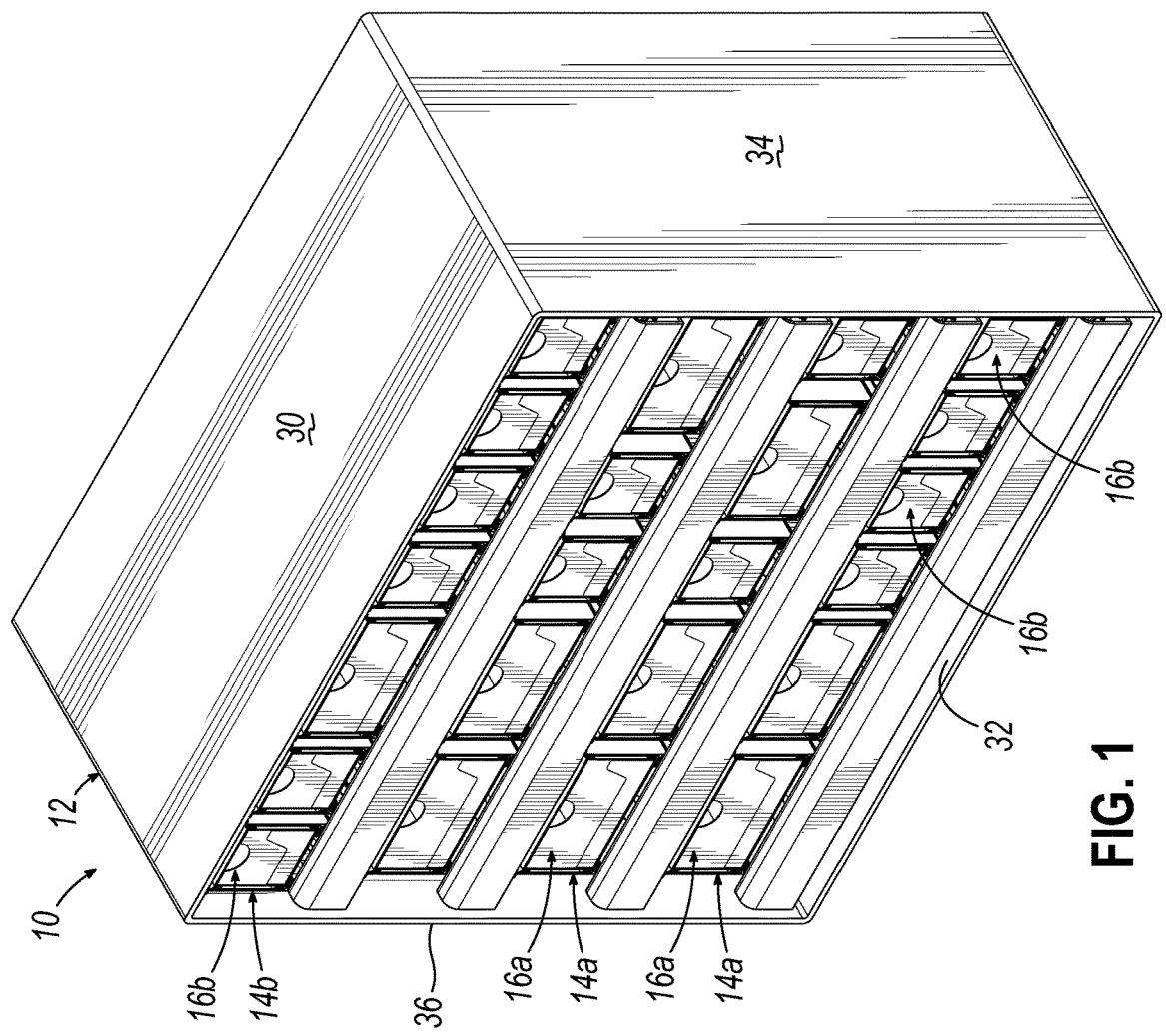
FIG. 1 is a perspective view of an exemplary storage system including a storage cabinet in accordance with an embodiment of the present invention.
Figure 3:
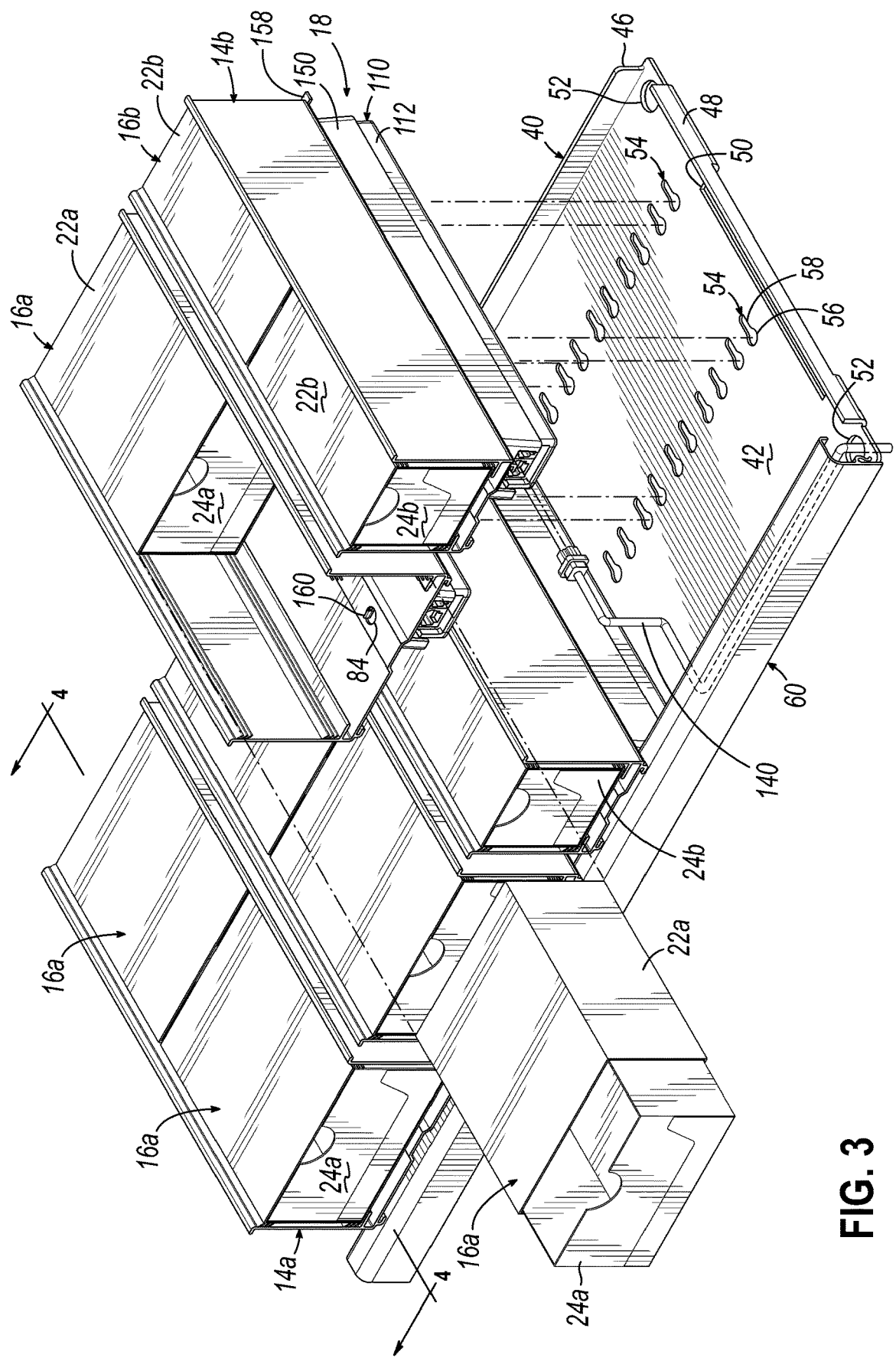
FIG. 3 is a schematic view of one of the shelves of FIG. 1, showing a plurality of suture holders and respective suture scales supported on the shelf, and further showing a plurality of suture boxes held by the suture holders.
Figure 4:
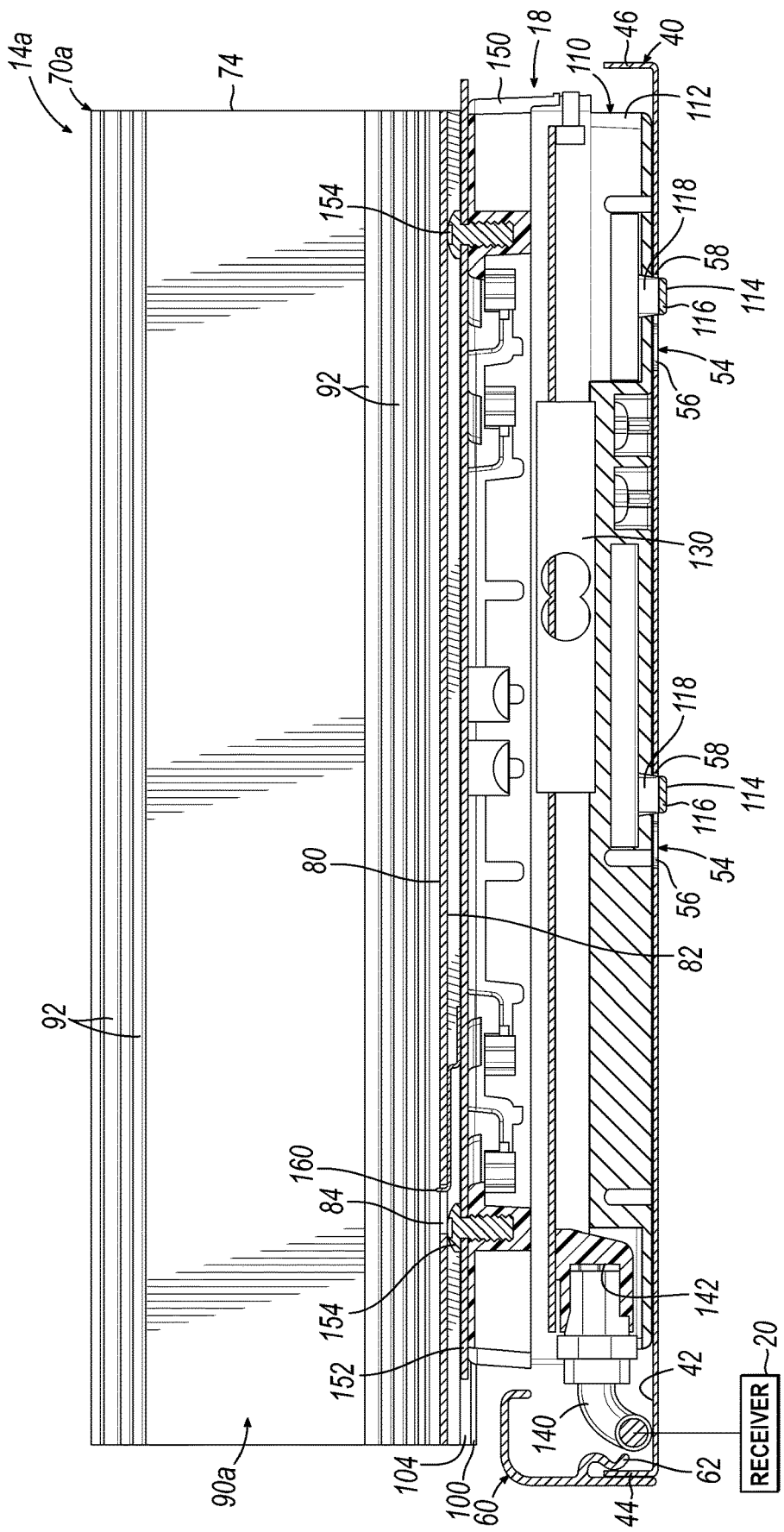
FIG. 4 is a cross sectional view of the shelf of FIG. 3, taken along section line 4-4, showing one of the suture holders locked in place relative to the respective suture scale with the suture box removed from the suture holder, and further showing a load sensor of the suture scale in operative communication with a receiver of the storage system.

With reference to FIGS. 1-3, an exemplary storage system 10 including a suture cabinet 12 is illustrated according to one embodiment of the present invention. The storage system 10 may be used to efficiently store and continuously monitor inventories of sutures in a suitable location, such as in a hospital or surgery center, and more particularly within a central operating room storage area, an individual operating room for a selected type of surgery, emergency department, or other area of the facility. As shown, the suture cabinet 12 houses a plurality of suture holders 14a, 14b configured to hold corresponding suture containers or boxes 16a, 16b, each containing individually wrapped sutures (not shown), for example. Each suture holder 14a, 14b may be capable of retaining any number of versions of industry standard suture boxes 16a, 16b. The suture holders 14a, 14b may be provided in a plurality of sizes, such as a large holder 14a and a small holder 14b for accommodating large and small suture boxes 16a, 16b, respectively. As described in greater detail below, each of the suture holders 14a, 14b is supported by a respective precision suture scale 18 configured to continuously measure the weight of the corresponding suture holder 14a, 14b and its contents and communicate the detected weight to a receiver 20 (FIG. 4). The detected weight may be used by the receiver 20 to continuously monitor an inventory of the suture holder 14a, 14b so that the inventories of the suture holders 14a, 14b may be appropriately replenished. In this manner, the storage system 10 may provide improved cost management by reducing overstocked or slow-moving inventory, and may also provide improved utilization of valuable space in the operating room core inventory areas and timely replenishment of consumed inventory to eliminate stock-outs and delays in surgical procedures resulting from lack of necessary inventory.

The suture boxes 16a, 16b described herein may be standard suture boxes. For example, the suture boxes 16a, 16b may be available in two primary sizes, such as a wide or large box 16a having dimensions of 4⅝16 inches wide by 2⅞16 inches high and 5½ inches long, and a narrow or small box 16b having dimensions of 2⅝16 inches wide by 2⅞16 inches high and 5½ inches long. Each of the suture boxes 16a, 16b may be constructed of thin cardstock, for example, and may contain between 12 and 36 individually wrapped sterile sutures. In one embodiment, each of the suture boxes 16a, 16b may be dedicated to a particular type of suture, and the sutures contained in a particular suture box 16a, 16b may have a generally uniform unit weight. In the embodiment shown, each of the suture boxes 16a, 16b includes an outer shell portion 22a, 22b and an inner drawer portion 24a, 24b configured to house the individually wrapped sutures and configured to be slidable relative to the outer shell portion 22a, 22b between an opened position for providing access to the individually wrapped sutures and a closed position for restricting access to the individually wrapped sutures. Thus, the suture boxes 16a, 16b may be considered to be of an international style. Alternatively, domestic style suture boxes (not shown) having a slot at a bottom of a shell portion for providing access to the individually wrapped sutures, or any other suitable suture boxes or other containers, may be used.

The illustrated suture cabinet 12 includes a top wall 30, a bottom wall 32, and first and second side walls 34, 36. In one embodiment, the suture cabinet 12 may have dimensions of 26 inches wide by 24 inches high and 13 inches deep. Mounting holes (not shown) may be provided in the walls 30, 32, 34, 36 which may allow the cabinet 12 to be fixedly mounted to one or more adjacent cabinets 12 in a stacked, side-by-side, or matrix configuration, for example, as described below. As best shown in FIG. 2, a plurality of generally hook-shaped shelf supports 38 are positioned on interior sides of the side walls 34, 36 and extend longitudinally therealong at various heights. Each shelf support 38 on the first side wall 34 is vertically aligned with a corresponding shelf support 38 on the second side wall 36 so that each pair of aligned shelf supports 38 may cooperate to support a shelf 40 at or near the ends thereof. In this manner, one or more shelves 40 may be selectively positioned at various vertical locations in the cabinet 12.

The shelves 40 may be vertically spaced apart from each other by suitable distances to accommodate items having various heights, such as the suture holders 14a, 14b, suture boxes 16a, 16b, and/or suture scales 18. In one embodiment, one or more of the shelves 40 may be removed from an original location in the cabinet 12 and repositioned at a new location in the cabinet 12 to adjust the vertical spacing of the shelves 40. Such modularity may allow a single cabinet 12 to be suitable for various applications regardless of changes in height of the items to be placed thereon. In one embodiment, the cabinet 12 may be configured to hold up to four shelves 40, for example.

As best shown in FIG. 3, each shelf 40 includes a support surface 42 for carrying one or more items, such as one or more of the suture holders 14a, 14b, suture boxes 16a, 16b, and/or suture scales 18. A front wall 44, a rear wall 46, and a pair of side walls 48 (one shown in FIG. 3) are provided at or near the periphery of the support surface 42 to assist in retaining items on the support surface 42. A pair of elongate recesses 50 (one shown in FIG. 3) are provided at or near the side walls 48 and are configured to receive the shelf supports 38 with the side walls 48 resting on the shelf supports 38 to secure the shelf 40 in place within the cabinet 12. A plurality of routing holes 52 and a plurality of mounting holes 54 are provided in the support surface 42 for purposes described below. In the embodiment shown, adjacent mounting holes 54 near a front end of the shelf 40 are spaced apart from each other by predetermined distances, and adjacent mounting holes 54 near a rear end of the shelf 40 are spaced apart from each other by predetermined distances and aligned with corresponding mounting holes 54 near the front end of the shelf 40. Each mounting hole 54 includes an enlarged portion 56 and a narrow portion 58, such that each mounting hole 54 is generally keyhole-shaped. As shown, a front guard or cover 60 is removably coupled to each shelf 40 at or near the front end thereof for assisting in retaining and/or concealing various items on the shelf 40, as described in greater detail below. In this regard, the illustrated cover 60 includes a spring clip 62 (FIG. 4) configured to releasably engage the front wall 44 of the shelf 40 for coupling the cover 60 to the shelf 40.

Referring now to FIGS. 4 and 5, with continuing reference to FIGS. 1-3, each exemplary large suture holder 14a includes a frame 70a having a bottom wall 72a and first and second side walls 74, 76 spaced apart from each other at top ends thereof to define an opening 78a, such that each frame 70a has a generally U-shaped cross section. The bottom wall 72a includes a longitudinally extending raised portion or ridge 80 defining a longitudinally extending bottom channel 82, the purpose of which is described below. At least one stop hole 84 is provided in the ridge 80 to assist in preventing the holder 14a from becoming inadvertently dislodged from the respective suture scale 18, as described in greater detail below. In one embodiment, the frame 70a is constructed of a plastic material. For example, the frame 70a may be constructed of extruded PVC.

In the embodiment shown, first and second box supports 86, 88 are positioned on interior sides of the side walls 74, 76 and extend longitudinally therealong at an aligned height so that the box supports 86, 88 may cooperate to support one or more of the suture boxes 16a, 16b at or near the sides thereof. The first and second side walls 74, 76, opening 78, and first and second box supports 86, 88 collectively define a main cavity 90a of the suture holder 14a, which is sized and configured to receive one or more of the suture boxes 16a, 16b. In the embodiment shown, the main cavity 90a of the large holder 14a is sized and configured to receive two of the large suture boxes 16a in an end-to-end arrangement, such that the large holder 14a may accommodate between 24 and 72 individual sutures. In this regard, the main cavity 90a may have a height and a width approximately equal to the height and width of one of the large suture boxes 16a, respectively, and may have a length approximately equal to twice the length of one of the large suture boxes 16a.

In one embodiment, each of the holders 14a, 14b may be dedicated to a particular type of suture. For example, the two suture boxes 16a, 16b held by a particular holder 14a, 14b may contain a same type of suture having a uniform unit weight, which may be different from the types of sutures contained in the suture boxes 16a, 16b held by the remaining holders 14a, 14b and having different uniform unit weights. In one embodiment, the cabinet 12 may be configured to contain between 16 and 32 different types of sutures, depending on the particular configuration of the cabinet 12. The FIFO (first in, first out) system may be employed in using and restocking the suture boxes 16a, 16b held by each of the holders 14a, 14b.

As best shown in FIG. 5, a plurality of resilient finger grips 92 are positioned on interior sides of the side walls 74, 76 and extend longitudinally therealong for frictionally engaging the one or more suture boxes 16a, 16b, such as the outer shell portion 22a, 22b thereof, to assist in preventing the one or more suture boxes 16a, 16b from becoming inadvertently dislodged from the main cavity 90a, such as when the inner drawer portion 24a, 24b is slid toward an opened position for accessing the individually wrapped sutures. The finger grips 92 may be constructed of a relatively soft (e.g., having a hardness of approximately 40 Shore A) plastic material, such as PVC. For example, the finger grips 92 may be coextruded with the frame 70a of the holder 14a such that the holder 14a is a unitary structure. Any other suitable material may be used for the finger grips 92, such as rubber. In the embodiment shown, the finger grips 92 are arranged in groups of three, which are positioned at or near the top and bottom ends of the first and second side walls 74, 76, such that the finger grips 92 may frictionally engage the respective box 16a, 16b in four locations (e.g., at or near the top and bottom ends of each side of the box 16a, 16b) to hold the box 16a, 16b in position. As shown, each of the finger grips 92 may be angled slightly downwardly from the respective side wall 74, 76 into the main cavity 90a to avoid interfering with insertion of the box 16a, 16b into the main cavity 90a via the opening 78a while resisting movement of the box 16a, 16b in upward and longitudinal directions.

In the embodiment shown, the bottom wall 72a, first and second side walls 74, 76, and first and second box supports 86, 88 collectively define an auxiliary cavity or storage slot 94a configured to receive loose unused sutures which have been removed from one of the respective boxes 16a, 16b, for example. In this regard, many hospitals and other institutions prohibit unused sutures from being returned to the original suture box 16a, 16b due to contamination concerns. The storage slot 94a provides a location to store such unused sutures for later use and prevents them from being unnecessarily discarded, thereby reducing waste.

As shown, first and second rails 100, 102 are positioned on an exterior side of the bottom wall 72a and extend longitudinally therealong, spaced apart from each other by a predetermined distance. The rails 100, 102 are each generally hook-shaped such that the bottom wall 72a and the first and second rails 100, 102 define first and second longitudinally extending grooves 104, 106, respectively, the purposes of which are described below.

As shown in FIG. 6, the configuration of the small suture holder 14b may be generally similar to that of the large suture holder 14a, with the primary exception being that the frame 70b of the small suture holder 14b includes a bottom wall 72b having a lesser width to accommodate the small suture box 16b, such that the opening 78b, cavity 90b, and storage slot 94b also have lesser widths relative to the large suture holder 14a.

With continuing reference to FIGS. 4-6, each exemplary suture scale 18 includes a base or chassis 110 including a support frame 112, which may be constructed of a plastic material. For example, the support frame 112 may be constructed of an injection molded plastic. In any event, the chassis 110 also includes a plurality of mounting feet 114 configured to mechanically engage the mounting holes 54 of one of the shelves 40 for securing the suture scale 18 to the shelf 40. In this regard, adjacent mounting feet 114 near a front end of the scale 18 are spaced apart from each other by a predetermined distance similar to the distance(s) between adjacent mounting holes 54 near the front end of the shelf 40, and adjacent mounting feet 114 near a rear end of the scale 18 are spaced apart from each other by a similar predetermined distance and aligned with the mounting feet 114 near the front end of the scale 18. Each of the mounting feet 114 includes an enlarged portion 116 and a narrow portion 118. The enlarged portion 116 of each mounting foot 114 may have a cross dimension similar to that of the enlarged portion 56 of each mounting hole 54, and the narrow portion 118 of each mounting foot 114 may have a cross dimension similar to that of the narrow portion 58 of each mounting hole 54. In this manner, the enlarged portion 116 of the foot 114 may be initially passed through the enlarged portion 56 of the hole 54, and the chassis 110 may be slid across the support surface 42 of the shelf 40 with the narrow portion 118 of the foot 114 received in the narrow portion 58 of the hole 54 to lock the chassis 110 in place on the support surface 42. Thus, one or more scales 18 may be selectively positioned at various horizontal locations along the shelves 40 in the cabinet 12.

The scales 18 may be horizontally spaced apart from each other on each shelf 40 by suitable distances to accommodate the suture holders 14a, 14b having various widths. In one embodiment, one or more of the scales 18 may be removed from an original location on the shelf 40 and repositioned at a new location on the shelf 40 to adjust the horizontal spacing of the scales 18. Such modularity may allow a single shelf 40 to be suitable for various applications regardless of changes in width of the suture holders 14a, 14b to be placed thereon. In one embodiment, each shelf 40 may be configured to hold up to four scales 18 carrying four large suture holders 14a, or up to eight scales 18 carrying eight small suture holders 14b, or various numbers of scales 18 carrying different varieties of large and small suture holders 14a, 14b.

In one embodiment, each of the covers 60 may assist in retaining the scales 18 on the respective shelves 40. For example, each cover 60 may be coupled to the respective shelf 40 after the shelf 40 has been populated with the desired scales 18 locked in place on the support surface 42 such that the cover 60 confronts the scales 18 to prevent the scales 18 from inadvertently moving forward and becoming unlocked from the support surface 42.

The chassis 110 also includes a mounting location for supporting a dedicated load sensor or load cell 130 configured to detect a precise weight, such as the weight of the respective suture holder 14a, 14b and the contents thereof, and to communicate the detected weight electronically via one or more signals to the receiver 20 in order to provide information indicative of the inventory status of the sutures contained in the box(es) 16a, 16b held by the holder 14a, 14b. In this regard, the load cell 130 may be of the strain gauge type. For example, the load cell 130 may include a beam and four strain gauges arranged in a Wheatstone bridge configuration and may be driven with an alternating current (AC) drive signal. The output of the load cell 130 may be amplified with a differential instrument amplifier and digitized by a precision 24 bit analog to digital convertor (ADC), for example. The output of the ADC may be a serial data stream which may be transmitted to the receiver 20 for processing, such as via a serial communications network. In one embodiment, the serial communications network may be facilitated by various data cables 140 operatively coupled to data ports 142 in communication with the load cells 130. The data cables 140 may be concealed by the cover 60 and directed through one of the routing holes 52 of the respective shelf 40 to a terminal (not shown) of the receiver 20. Alternatively, the serial communications network may be facilitated by a wireless connection, for example.

In one embodiment, each of the load cells 130 is calibrated to account for the removal of individually wrapped sutures. For example, when one or more individual sutures are removed from the corresponding suture holder 14a, 14b, the load cell 130 may be configured to identify a change in weight of the corresponding suture holder 14a, 14b. The change in weight may be communicated to the receiver 20, and the receiver 20 may infer that one or more sutures have been removed from the suture holder 14a, 14b based on the change in weight. For example, a decrease in the weight measured by the load cell 130 by one unit weight may indicate that one individual suture has been removed from the suture holder 14a, 14b, while a decrease in the weight measured by the load cell 130 by two unit weights may indicate that two individual sutures have been removed from the suture holder 14a, 14b. Since the storage slot 94a, 94b is included in the holder 14a, 14b, any loose sutures that have been placed in the storage slot 94a, 94b may be accounted for by the load cell 130.

In one embodiment, the receiver 20 may continuously display the current inventory quantity at a monitoring station, for example. In addition or alternatively, when a predetermined target weight of the suture holder 14a, 14b is reached, the receiver 20 may display a message at the monitoring station to signal that the inventory of the suture holder 14a, 14b should be replenished. The monitoring station may be on site or physically remote from the location of the cabinet 12. In one embodiment, the monitoring station may be incorporated into a comprehensive inventory management system, such as that which is commercially available under the trademark PAR Excellence.

The exemplary suture scale 18 also includes a scale platform 150 positioned over and carried by the load cell 130. The scale platform 150 may be constructed of a plastic material. For example, the scale platform 150 may be constructed of an injection molded plastic. In any event, a suture holder support plate 152 is positioned over and carried by the platform 150 for supporting the suture holder 14a, 14b. As shown, the support plate 152 is secured to the platform 150 via one or more fasteners 154. In this manner, the weight load of the suture holder 14a, 14b and its contents may be transferred to the load cell 130 via the scale platform 150 and the suture holder support plate 152. As best shown in FIG. 5, the support plate 152 may have a width similar to the distance between the rails 100, 102 of the suture holder 14a, 14b and may have a thickness similar to a width of each of the grooves 104, 106 of the suture holder 14a, 14b, such that the grooves 104, 106 of the suture holder 14a, 14b may slidably engage the side edges of the support plate 152. Thus, the suture holder 14a, 14b may longitudinally slide along the support plate 152 in forward and reverse directions while remaining securely retained on the support plate 152. For example, the suture holder 14a, 14b may slide in a forward direction to provide convenient access to the main cavity 90a, 90b thereof via the opening 78a, 78b, such as for restocking or maintenance purposes, and may be subsequently slid in a reverse direction to return to its original position.

In the embodiment shown, first and second stop tabs 156, 158 are provided at or near the rear ends of the sides of the support plate 152 for abutting the first and second rails 100, 102 of the holder 14a, 14b to thereby limit sliding movement of the suture holder 14a, 14b relative to the support plate 152 in the reverse direction. In this manner, the interaction of the stop tabs 156, 158 with the rails 100, 102 may assist in preventing the holder 14a, 14b from being inadvertently dislodged from the scale 18. As shown, a flexible spring tab 160 is located on the top of the support plate 152 generally proximate a front end thereof. The flexible spring tab 160 is configured to flex into the stop hole 84 of the suture holder 14a, 14b when aligned therewith to mechanically engage with the periphery of the stop hole 84 and thereby limit sliding movement of the suture holder 14a, 14b relative to the support plate 152 in the forward direction. In this manner, the interaction of the stop hole 84 with the flexible spring tab 160 may assist in preventing the holder 14a, 14b from being inadvertently dislodged from the scale 18. In one embodiment, the flexible spring tab 160 may be manually depressed in order to disengage the periphery of the stop hole 84 so that the holder 14a, 14b may be completely removed from the scale 18, such as for maintenance purposes. During normal sliding movement of the holder 14a, 14b relative to the scale 18, the bottom channel 82 of the holder 14a, 14b may accommodate the fasteners 154 and/or spring tab 160 to allow sliding of the holder 14a, 14b to occur in a smooth manner.

In one embodiment, the receiver 20 may collect and store data relating to the inventory condition of the suture box(es) 16a, 16b held by each holder 14a, 14b. The inventory condition may be determined based on a pre-loaded program which sets the maximum weight of the corresponding suture box(es) 16a, 16b less the tare weight of the box(es) 16a, 16b, holder 14a, 14b, platform 150, and/or plate 152 in order to accurately determine the inventory condition in response to the weight detected by the respective load cell 130.

Figure 7:
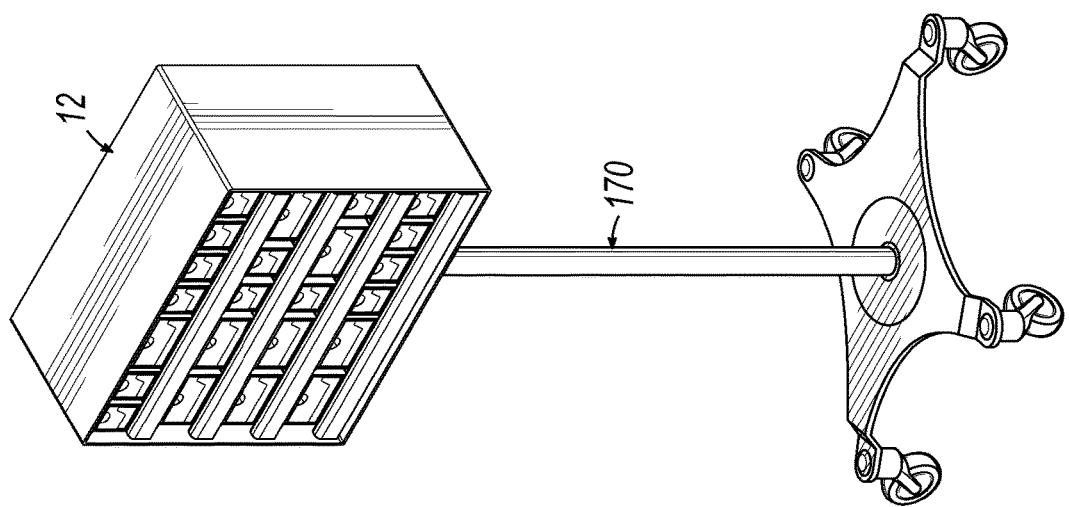
FIG. 7 is a perspective view of an alternative storage system wherein the cabinet is mounted on a mobile cart.

Referring now to FIG. 7, the cabinet 12 may be mounted on a mobile cart 170 such that the cabinet 12 and contents thereof may be readily movable across a surface such as a hospital floor. In this manner, the sutures held by the holders 14a, 14b may be deployed directly into the procedure area of the hospital, for example. In one embodiment, the cart 170 may be configured to contain between 16 and 64 different types of sutures, depending on the particular configuration of the cabinet 12. The cart 170 may also carry an onboard battery and/or WiFi controller (not shown) so that the suture scales 18 may be continuously monitored during transit of the cart 170 without interruption. In addition or alternatively, the cart 170 may be equipped with clear protective door panels (not shown) to prevent contamination of the sutures held by the holders 14a, 14b in procedure areas.

Figure 8:
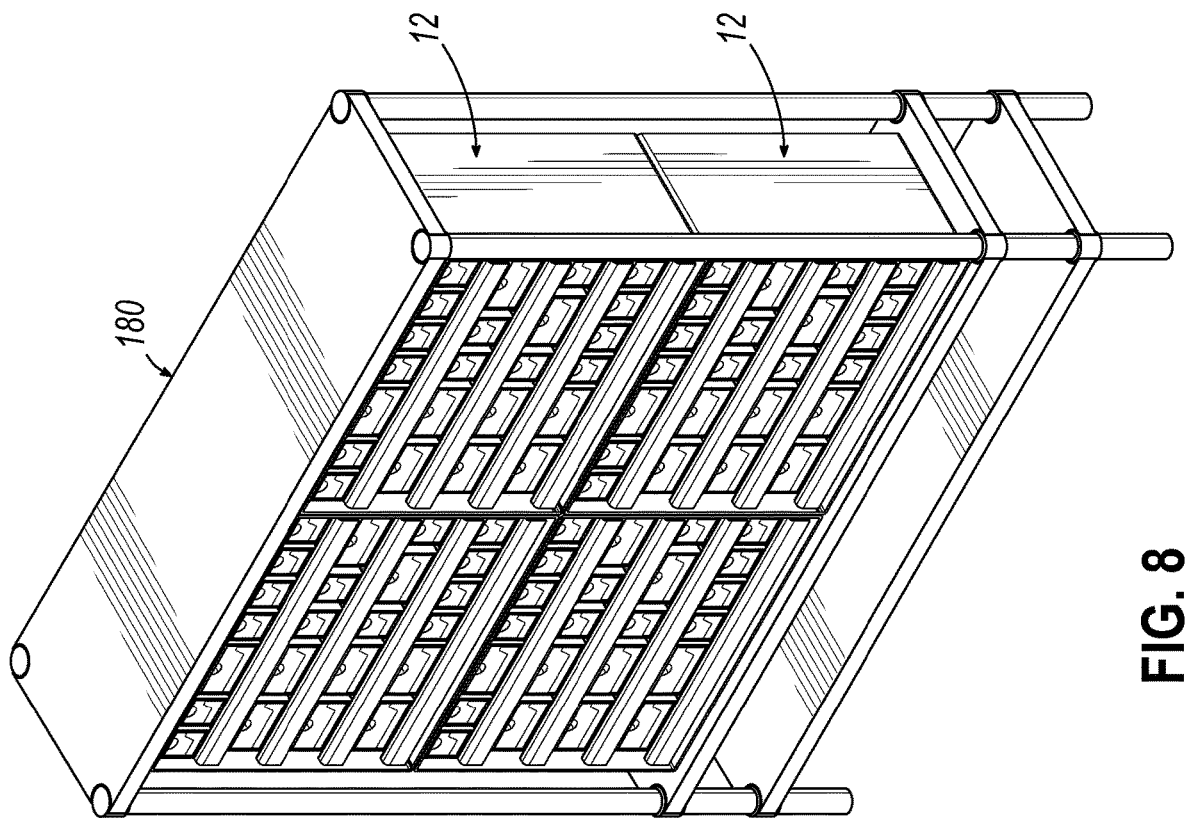
FIG. 8 is a perspective view of an alternative storage system wherein a plurality of cabinets are positioned on a rack.

Referring now to FIG. 8, a plurality of cabinets 12 may be mounted on a rack 180. As shown, the cabinets 12 may be stacked vertically and horizontally. In addition or alternatively, the cabinets 12 may be interconnected or coupled together.

Figure 9:
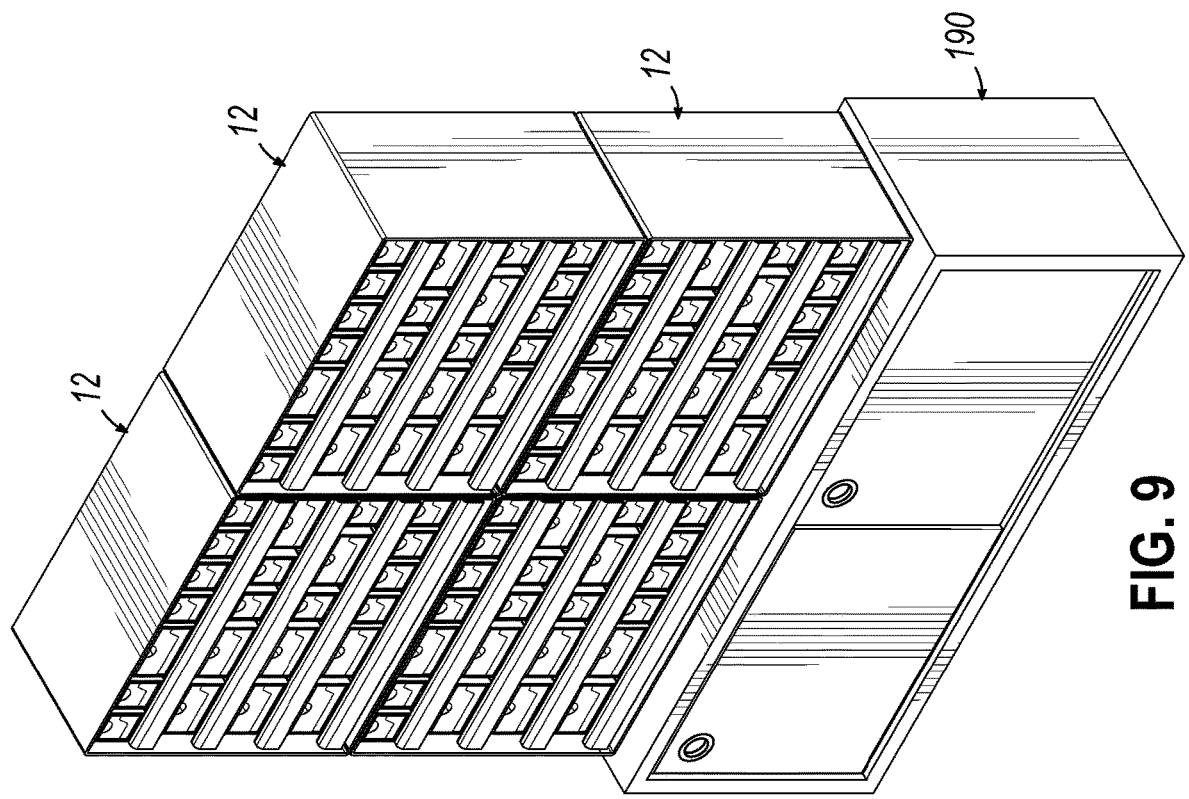
FIG. 9 is a perspective view of an alternative storage system wherein a plurality of cabinets are interconnected in a matrix and positioned on a stand.

Referring now to FIG. 9, a plurality of cabinets 12 may be interconnected or coupled together to form a bulk storage arrangement or matrix of cabinets 12, such as for fulfilling large storage requirements. In the embodiment shown, the matrix of cabinets 12 is positioned on a table or stand 190.

In another embodiment, one or more louver mounting brackets (not shown) may be used to allow a plurality of cabinets 12 to be installed on wall louver panels.

Figure 10:
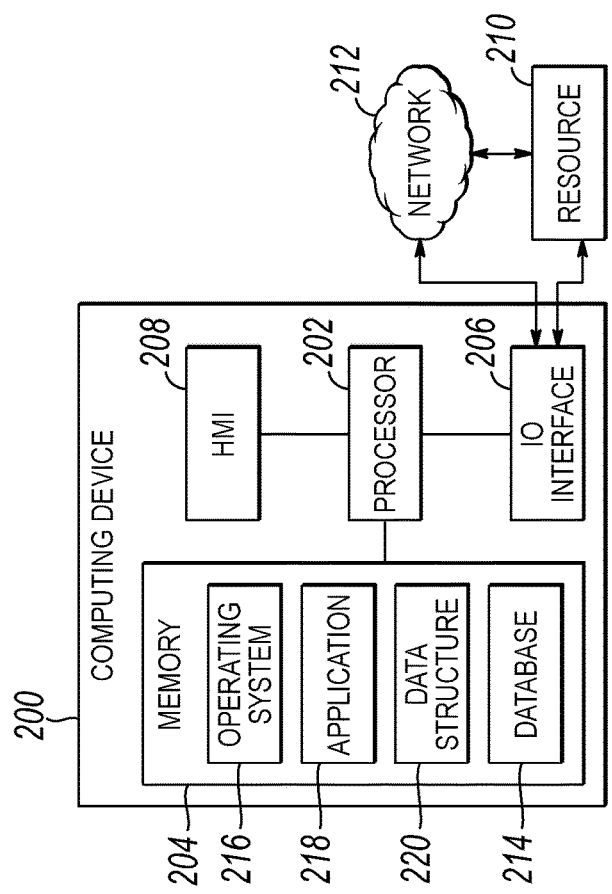
FIG. 10 is a block diagram for the relationship between the computing device, the resource, and the network through which information flows.

Referring to FIG. 10, the embodiments of the invention described above relating to the interface between each of the signal-generating load cells 130 and a receiver 20 and/or monitoring station may be implemented using one or more computer devices or systems, such as an exemplary computer system 200. The computer system 200 may include a processor 202, a memory 204, a mass storage memory device, an input/output (I/O) interface 206, and a user interface 208. The computer system 200 may also be operatively coupled to one or more external resources 210 via the I/O interface 206 and/or a network 212.

The processor 202 may include one or more devices selected from microprocessors, micro-controllers, digital signal processors, microcomputers, central processing units, field programmable gate arrays, programmable logic devices, state machines, logic circuits, analog circuits, digital circuits, or any other devices that manipulate signals (analog or digital) based on operational instructions that are stored in the memory 204. Memory 204 may include a single memory device or a plurality of memory devices including but not limited to read-only memory (ROM), random access memory (RAM), volatile memory, non-volatile memory, static random access memory (SRAM), dynamic random access memory (DRAM), flash memory, cache memory, or any other device capable of storing information. The mass storage memory device may include data storage devices such as a hard drive, optical drive, tape drive, non-volatile solid state device, or any other device capable of storing information. A database 214 may reside on the mass storage memory device, and may be used to collect and organize data used by the various systems and modules described herein.

The processor 202 may operate under the control of an operating system 216 that resides in memory 204. The operating system 216 may manage computer resources so that computer program code embodied as one or more computer software applications, such as application 218 residing in memory 204 may have instructions executed by the processor 202. In an alternative embodiment, the processor 202 may execute the applications directly, in which case the operating system 216 may be omitted. One or more data structures 220 may also reside in memory 204, and may be used by the processor 202, operating system 216, and/or application 218 to store or manipulate data.

The I/O interface 206 may provide a machine interface that operatively couples the processor 202 to other devices and systems, such as the network 212 and/or external resource 210. The application 218 may thereby work cooperatively with the network 212 and/or external resource 210 by communicating via the I/O interface to provide the various features, functions, and/or modules comprising embodiments of the invention. The application 218 may also have program code that is executed by one or more external resources 210, or otherwise rely on functions and/or signals provided by other system or network components external to the computer system 200. Indeed, given the nearly endless hardware and software configurations possible, persons having ordinary skill in the art will understand that embodiments of the invention may include applications that are located externally to the computer system 200, distributed among multiple computers or other external resources, or provided by computing resources (hardware and software) that are provided as a service over the network 212, such as a cloud computing service.

The user interface 208 may be operatively coupled to the processor 202 of computer system 200 in a known manner to allow a user to interact directly with the computer system 200. The user interface 208 may include video and/or alphanumeric displays, a touch screen, a speaker, and any other suitable audio and visual indicators capable of providing information to the user. The user interface 208 may also include input devices and controls such as an alphanumeric keyboard, a pointing device, keypads, pushbuttons, control knobs, microphones, etc., capable of accepting commands or input from the user and transmitting the entered input to the processor 202.

In general, the routines executed to implement the embodiments of the invention, whether implemented as part of an operating system or a specific application, component, program, object, module or sequence of instructions, or a subset thereof, may be referred to herein as "computer program code," or simply "program code." Program code typically comprises computer-readable instructions that are resident at various times in various memory and storage devices in a computer and that, when read and executed by one or more processors in a computer, cause that computer to perform the operations necessary to execute operations and/or elements embodying the various aspects of the embodiments of the invention. Computer-readable program instructions for carrying out operations of the embodiments of the invention may be, for example, assembly language or either source code or object code written in any combination of one or more programming languages.

Various program code described herein may be identified based upon the application within which it is implemented in specific embodiments of the invention. However, it should be appreciated that any particular program nomenclature which follows is used merely for convenience, and thus the invention should not be limited to use solely in any specific application identified and/or implied by such nomenclature. Furthermore, given the generally endless number of manners in which computer programs may be organized into routines, procedures, methods, modules, objects, and the like, as well as the various manners in which program functionality may be allocated among various software layers that are resident within a typical computer (e.g., operating systems, libraries, API's, applications, applets, etc.), it should be appreciated that the embodiments of the invention are not limited to the specific organization and allocation of program functionality described herein.

The program code embodied in any of the applications/modules described herein is capable of being individually or collectively distributed as a program product in a variety of different forms. In particular, the program code may be distributed using a computer-readable storage medium having computer-readable program instructions thereon for causing a processor to carry out aspects of the embodiments of the invention.

Computer-readable storage media, which is inherently non-transitory, may include volatile and non-volatile, and removable and non-removable tangible media implemented in any method or technology for storage of data, such as computer-readable instructions, data structures, program modules, or other data. Computer-readable storage media may further include RAM, ROM, erasable programmable read-only memory (EPROM), electrically erasable programmable read-only memory (EEPROM), flash memory or other solid state memory technology, portable compact disc read-only memory (CD-ROM), or other optical storage, magnetic cassettes, magnetic tape, magnetic disk storage or other magnetic storage devices, or any other medium that can be used to store the desired data and which can be read by a computer. A computer-readable storage medium should not be construed as transitory signals per se (e.g., radio waves or other propagating electromagnetic waves, electromagnetic waves propagating through a transmission media such as a waveguide, or electrical signals transmitted through a wire). Computer-readable program instructions may be downloaded to a computer, another type of programmable data processing apparatus, or another device from a computer-readable storage medium or to an external computer or external storage device via a network.

Computer-readable program instructions stored in a computer-readable medium may be used to direct a computer, other types of programmable data processing apparatuses, or other devices to function in a particular manner, such that the instructions stored in the computer-readable medium produce an article of manufacture including instructions that implement the functions, acts, and/or operations specified in the flow-charts, sequence diagrams, and/or block diagrams. The computer program instructions may be provided to one or more processors of a general purpose computer, a special purpose computer, or other programmable data processing apparatus to produce a machine, such that the instructions, which execute via the one or more processors, cause a series of computations to be performed to implement the functions, acts, and/or operations specified in the flow-charts, sequence diagrams, and/or block diagrams.

In certain alternative embodiments, the functions, acts, and/or operations specified in the flow-charts, sequence diagrams, and/or block diagrams may be re-ordered, processed serially, and/or processed concurrently consistent with embodiments of the invention. Moreover, any of the flow-charts, sequence diagrams, and/or block diagrams may include more or fewer blocks than those illustrated consistent with embodiments of the invention.

The terminology used herein is for the purpose of describing particular embodiments only and is not intended to be limiting of the embodiments of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, actions, steps, operations, elements, and/or components, but do not preclude the presence or addition of one or more other features, integers, actions, steps, operations, elements, components, and/or groups thereof. Furthermore, to the extent that the terms "includes", "having", "has", "with", "comprised of", or variants thereof are used in either the detailed description or the claims, such terms are intended to be inclusive in a manner similar to the term "comprising".

The holder 14a, 14b described herein is capable of storing boxes 16a, 16b of standardized dimension and weight, retained in place within the holder 14a, 14b by the finger grips 92, and the removal of sutures from the box 16a, 16b can be monitored by the load cell 130. This information can then be conveyed to a monitoring station via the receiver 20 to provide an inventory status to facilitate timely restocking.

While the suture holders 14a, 14b and scales 18 have been shown and described as being mounted on the respective shelves 40 in a generally horizontal orientation, it will be appreciated that the suture holders 14a, 14b and scales 18 may be mounted in any suitable orientation. For example, one or more holders 14a, 14b and respective scales 18 may be mounted at an angle of 45° relative to horizontal, such as to retrofit a pre-existing sloping suture shelving system or cart with the holders 14a, 14b and scales 18. In such cases, the scales 18 may be calibrated at the same angle relative to horizontal, such as 45°, so that the sloped orientation of the scales 18 during calibration may compensate for weight errors that may otherwise occur if the scales 18 were calibrated in a generally horizontal orientation.

Although the storage system 10 including the cabinet 12, holders 14a, 14b, scales 18, and shelves 40 have been described herein in relation to the storage and monitoring of inventories of sutures, it will be appreciated that the storage system 10 and/or components thereof may be used to store and monitor any other type of inventory. For example, the storage system 10 may be used for storing and monitoring inventories of other medical supplies provided in standard-sized packaging and having generally uniform unit weights, such as intraocular implants, endomechanical devices, and orthopedic devices.

While the present invention has been illustrated by the description of various embodiments thereof, and while these embodiments have been described in considerable detail, it is not intended to restrict or in any way limit the scope of the appended claims to such detail. Thus, the various features discussed herein may be used alone or in any combination. Additional advantages and modifications will readily appear to those skilled in the art. The present invention in its broader aspects is therefore not limited to the specific details and illustrative examples shown and described. Accordingly, departures may be made from such details without departing from the scope of the general inventive concept.

What is claimed is:

1. A storage system, comprising:
   at least one cabinet;
   a plurality of shelves adjustably positioned within the at least one cabinet;
   a plurality of scales removably attached to at least one of the shelves, each of the scales including a load sensor;
   a plurality of holders, each of the holders being configured to hold at least one container containing medical supplies, each of the holders being supported by a respective one of the scales, and each of the holders being longitudinally slidable relative to the respective scale;
   a plurality of support plates, each of the support plates being supported by a respective one of the scales, wherein each of the holders slidably receives the respective support plate; and
   a receiver in operative communication with each of the load sensors,
   wherein each of the load sensors is configured to continuously measure a weight of the medical supplies contained in the respective at least one container held by the respective holder, and to communicate each detected weight to the receiver.

2. The storage system of claim 1, wherein the receiver is configured to monitor an inventory condition of the medical supplies contained in each of the at least one container held by each holder in response to each detected weight.

3. The storage system of claim 2, wherein the receiver is configured to display the inventory condition to a monitoring station.

4. A storage system, comprising:
   at least one cabinet;
   a plurality of shelves adjustably positioned within the at least one cabinet;
   a plurality of scales removably attached to at least one of the shelves, each of the scales including a load sensor;
   a plurality of holders, each of the holders being configured to hold at least one container containing medical supplies, and each of the holders being supported by a respective one of the scales; and
   a receiver in operative communication with each of the load sensors,
   wherein each of the load sensors is configured to continuously measure a weight of the medical supplies contained in the respective at least one container held by the respective holder, and to communicate each detected weight to the receiver,
   wherein either each of the holders includes a plurality of longitudinally extending resilient finger grips for frictionally engaging the respective at least one container or each of the scales includes a plurality of mounting feet and each of the shelves includes a plurality of mounting holes, each of the mounting holes being configured to receive a respective one of the mounting feet.

5. The storage system of claim 1, wherein each of the holders includes a storage slot configured to receive one or more of the medical supplies which have been removed from the respective at least one container.

6. The storage system of claim 1, wherein each of the holders includes a stop hole and each of the support plates includes a flexible tab configured to releasably engage the stop hole of the respective holder for limiting longitudinal sliding of the respective holder relative to the respective scale.

7. The storage system of claim 1, wherein the plurality of holders includes a first plurality of holders each having a first width, and a second plurality of holders each having a second width less than the first width.

8. The storage system of claim 1, wherein the at least one cabinet is mounted to a mobile cart.

9. The storage system of claim 1, wherein the at least one cabinet includes a plurality of cabinets mounted on a rack.

10. The storage system of claim 1, wherein the at least one cabinet includes a plurality of cabinets interconnected in a matrix and mounted on a stand.

11. The storage system of claim 4, wherein the receiver is configured to monitor an inventory condition of the medical supplies contained in each of the at least one container held by each holder in response to each detected weight.

12. The storage system of claim 11, wherein the receiver is configured to display the inventory condition to a monitoring station.

13. The storage system of claim 11, wherein the at least one cabinet is mounted to a mobile cart.

* * * * *